United States Patent
Park et al.

(10) Patent No.: US 11,680,040 B2
(45) Date of Patent: Jun. 20, 2023

(54) COMPOUND, PHOTORESIST COMPOSITION COMPRISING SAME, PHOTORESIST PATTERN COMPRISING SAME, AND METHOD FOR MANUFACTURING PHOTORESIST PATTERN

(71) Applicant: LG CHEM, LTD., Seoul (KR)

(72) Inventors: Hyunmin Park, Daejeon (KR); Minyoung Lim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 376 days.

(21) Appl. No.: 16/978,557

(22) PCT Filed: Oct. 11, 2019

(86) PCT No.: PCT/KR2019/013364
§ 371 (c)(1),
(2) Date: Sep. 4, 2020

(87) PCT Pub. No.: WO2020/076122
PCT Pub. Date: Apr. 16, 2020

(65) Prior Publication Data
US 2021/0017127 A1 Jan. 21, 2021

(30) Foreign Application Priority Data
Oct. 11, 2018 (KR) .................. 10-2018-0120977

(51) Int. Cl.
| | |
|---|---|
| *C07C 309/12* | (2006.01) |
| *C07C 323/61* | (2006.01) |
| *C07C 323/62* | (2006.01) |
| *C07C 381/12* | (2006.01) |
| *G03F 7/004* | (2006.01) |
| *G03F 7/032* | (2006.01) |
| *G03F 1/42* | (2012.01) |
| *C08F 32/08* | (2006.01) |

(52) U.S. Cl.
CPC .......... *C07C 309/12* (2013.01); *C07C 323/62* (2013.01); *C07C 381/12* (2013.01); *C08F 32/08* (2013.01); *G03F 1/42* (2013.01); *G03F 7/0045* (2013.01); *G03F 7/032* (2013.01); *C07C 2602/42* (2017.05); *C07C 2603/74* (2017.05)

(58) Field of Classification Search
None
See application file for complete search history.

(56) References Cited

U.S. PATENT DOCUMENTS

| | | | |
|---|---|---|---|
| 7,527,912 B2 | 5/2009 | Ohsawa et al. | |
| 8,900,797 B2 | 12/2014 | Nakasugi et al. | |
| 8,932,795 B2 | 1/2015 | Seshimo et al. | |
| 2008/0085469 A1* | 4/2008 | Ohsawa ............... | C07D 491/18 548/530 |
| 2009/0233223 A1* | 9/2009 | Tachibana ............ | G03F 7/0045 430/296 |
| 2011/0287362 A1* | 11/2011 | Seshimo .............. | C07D 333/76 549/13 |
| 2013/0280657 A1 | 10/2013 | Kasahara et al. | |
| 2013/0280658 A1 | 10/2013 | Maruyama | |
| 2019/0243244 A1 | 8/2019 | Kaneko et al. | |

FOREIGN PATENT DOCUMENTS

| | | | | |
|---|---|---|---|---|
| JP | 2005092053 A | * | 4/2005 | |
| JP | 2013-092618 A | | 5/2013 | |
| JP | 2016-085382 A | | 5/2016 | |
| JP | 2017102267 A | * | 6/2017 | |
| JP | 2017-227810 A | | 12/2017 | |
| JP | 2018058824 A | * | 4/2018 | |
| KR | 10-1035742 B | | 5/2011 | |
| KR | 10-2011-0127601 A | | 11/2011 | |
| KR | 10-1673890 B1 | | 11/2016 | |
| KR | 10-1813298 B1 | | 12/2017 | |
| WO | WO-2011104127 A1 | * | 9/2011 | ............ C07C 25/18 |
| WO | 2012-070548 A1 | | 5/2012 | |
| WO | 2018-070327 A | | 4/2018 | |

OTHER PUBLICATIONS

International Search Report issued for International Application No. PCT/KR2019/013364 dated Jan. 21, 2020, 6 pages.

\* cited by examiner

*Primary Examiner* — Martin J Angebranndt
(74) *Attorney, Agent, or Firm* — Rothwell, Figg, Ernst & Manbeck, P.C.

(57) ABSTRACT

The present specification provides a compound, a photoresist composition comprising the same, a photoresist pattern comprising the same, and a method for preparing a photoresist pattern.

14 Claims, No Drawings

COMPOUND, PHOTORESIST COMPOSITION COMPRISING SAME, PHOTORESIST PATTERN COMPRISING SAME, AND METHOD FOR MANUFACTURING PHOTORESIST PATTERN

CROSS-REFERENCE TO RELATED APPLICATIONS

This application is a 35 U.S.C. 371 National Phase Entry Application from PCT/KR2019/013364 filed on Oct. 11, 2019, designating the United States, which claims priority to and the benefits of Korean Patent Application No. 10-2018-0120977, filed with the Korean Intellectual Property Office on Oct. 11, 2018, the entire contents of which are incorporated herein by reference.

TECHNICAL FIELD

The present specification relates to a compound, a photoresist composition comprising the same, and a method for preparing a pattern.

BACKGROUND OF THE INVENTION

A photoresist composition is used in, for example, a process of a microelectronic device for manufacturing small electronic components when manufacturing computer chips and integrated circuits. A process of a microelectronic device using a substrate material such as a silicon-based wafer used for manufacturing an integrated circuit is generally as follows.

A photoresist layer of a thin coating film is formed on a substrate using a photoresist composition or a photoresist film, and then the result is baked to fix the coating film on the substrate. The coating film fixed on the substrate is image-wise exposed to radiation. The exposed coating film is treated with a developing solution, and by dissolving and removing the exposed area or the unexposed area of the photoresist, a microelectronic device is formed.

High integration of a semiconductor has been advanced along with the development of photolithography technologies unmatched by other patterning techniques in terms of performance, reliability, and human and physical infrastructures.

Particularly, as a shorter light source and a matching photochemical reaction photoresist are used, the degree of device integration has rapidly increased with the development of KrF excimer laser (248 nm) and ArF laser (193 nm) lithography technologies using a high sensitivity chemical amplification-type photoresist.

Although 193i lithography technology has advanced to a level of progressing a process of manufacturing a device having a minimum line width of mid/late 10 nm through quadruple patterning, the process may not be generally used due to very high process costs and limited obtainable pattern shapes, and the resolution of 16 nm is recognized as a threshold. Extreme ultraviolet rays (EUV) have been predicted as an only technology capable of several nm patterning so far, however, the resolution of 12 nm is recognized as a threshold as well in this case due to an absence of a high resolution photoresist.

In order to overcome such a limit, attempts to develop an extreme ultraviolet photoresist have been actively made, however, there are problems to resolve such as improving sensitivity decrease, resolution and line width roughness (LWR).

BRIEF SUMMARY OF THE INVENTION

The present specification is directed to providing a compound, a photoresist composition comprising the same, a photoresist pattern comprising the same, and a method for preparing a photoresist pattern.

One embodiment of the present application provides a compound represented by the following Chemical Formula 1.

[Chemical Formula 1]

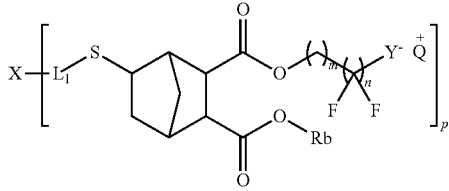

In Chemical Formula 1, p is an integer of 2 to 4, when p is 2 or greater, substituents in the parentheses are the same as or different from each other, when p is 2, X is S; a substituted or unsubstituted aryl group; a substituted or unsubstituted heteroaryl group; or a substituted or unsubstituted alkyl group, when p is an integer of 3 or 4, X is a substituted or unsubstituted aryl group; a substituted or unsubstituted heteroaryl group; or a substituted or unsubstituted alkyl group, $L_1$ is a direct bond; a substituted or unsubstituted alkylene group; a substituted or unsubstituted arylene group; or a substituted or unsubstituted heteroarylene group, Rb is a substituted or unsubstituted alkyl group; a substituted or unsubstituted cycloalkyl group; a substituted or unsubstituted aryl group; or a substituted or unsubstituted heteroaryl group, $Q^+$ is an onium cation, $Y^-$ is an acid anion, and m and n are an integer of 1 to 10.

Another embodiment of the present application provides a photoresist composition comprising the compound according to the present application; a binder resin; and a solvent.

Another embodiment of the present application provides a photoresist pattern comprising the photoresist composition according to the present application.

Lastly, one embodiment of the present application provides a method for preparing a photoresist pattern, the method comprising forming a photoresist layer by coating the photoresist composition of the present application on a semiconductor substrate; selectively exposing the photoresist layer; and developing the exposed photoresist layer.

Advantageous Effects

A compound according to one embodiment of the present application is a material having increased solubility for an alkali developing solution by being dissociated by an acid, and is capable of obtaining high resolution.

The compound according to one embodiment of the present application comprises a photoacid generator (PAG)

in the structure as in Chemical Formula 1, and is thereby capable of further enhancing contrast of an exposed portion and an unexposed portion in a photoresist process afterward, and is also capable of improving line width roughness (LWR) without reducing sensitivity.

In addition, a photoresist composition comprising the compound according to the present application is capable of high resolution and freely forming pattern shapes by comprising the compound.

In addition, the photoresist composition comprising the compound according to the present application is formed with monomers, and has improved line width roughness (LWR) since the resin in the photoresist is formed with monomers instead of polymers.

DETAILED DESCRIPTION OF THE INVENTION

Hereinafter, the present specification will be described in more detail.

In the present specification, a description of a certain part "including" certain constituents means capable of further comprising other constituents, and does not exclude other constituents unless particularly stated on the contrary.

Embodiments of the present disclosure will be described in detail with reference to accompanying drawings so that those skilled in the art may readily implement the present disclosure. However, the present disclosure may be embodied in various different forms, and is not limited to the embodiments described herein.

One embodiment of the present specification provides a compound represented by Chemical Formula 1.

[Chemical Formula 1]

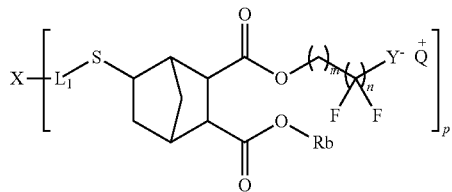

In Chemical Formula 1, p is an integer of 2 to 4, when p is 2 or greater, substituents in the parentheses are the same as or different from each other, when p is 2, X is S; a substituted or unsubstituted aryl group; a substituted or unsubstituted heteroaryl group; or a substituted or unsubstituted alkyl group, when p is an integer of 3 or 4, X is a substituted or unsubstituted aryl group; a substituted or unsubstituted heteroaryl group; or a substituted or unsubstituted alkyl group, L₁ is a direct bond; a substituted or unsubstituted alkylene group; a substituted or unsubstituted arylene group; or a substituted or unsubstituted heteroarylene group, Rb is a substituted or unsubstituted alkyl group; a substituted or unsubstituted cycloalkyl group; a substituted or unsubstituted aryl group; or a substituted or unsubstituted heteroaryl group, Q⁺ is an onium cation, Y⁻ is an acid anion, and m and n are an integer of 1 to 10.

The compound according to one embodiment of the present application is a material having increased solubility for an alkali developing solution by being dissociated by an acid, and is capable of obtaining high resolution, and, by including a photoacid generator (PAG) in the structure as in Chemical Formula 1, is capable of further enhancing contrast of an exposed portion and an unexposed portion in a photoresist process afterward, and is also capable of improving line width roughness (LWR) without reducing sensitivity.

Examples of substituents in the present specification are described below, however, the substituents are not limited thereto.

The term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the term "substituted or unsubstituted" means being substituted with one, two or more substituents selected from the group consisting of a halogen group; a nitrile group; an imide group; an amide group; a carbonyl group; an ester group; a hydroxyl group; a carboxyl group (—COOH); a sulfonic acid group (-SO₃H); a substituted or unsubstituted alkyl group; a substituted or unsubstituted cycloalkyl group; a substituted or unsubstituted alkoxy group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; and a substituted or unsubstituted heterocyclic group, or being substituted with a substituent linking two or more substituents among the substituents illustrated above, or having no substituents. For example, "a substituent linking two or more substituents" may comprise a biphenyl group. In other words, a biphenyl group may be an aryl group, or interpreted as a substituent linking two phenyl groups.

In the present specification,

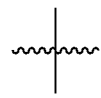

means a site bonding to other substituents or bonding sites.

In the present specification, the halogen group may comprise fluorine, chlorine, bromine or iodine.

In the present specification, the number of carbon atoms of the imide group is not particularly limited, but is preferably from 1 to 30. Specifically, compounds having structures as below may be included, however, the imide group is not limited thereto.

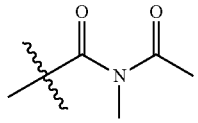

-continued

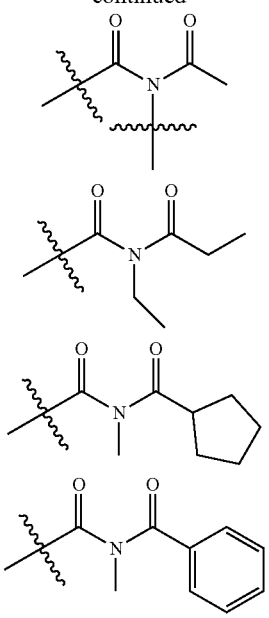

In the present specification, in the amide group, the nitrogen of the amide group may be substituted with a linear, branched or cyclic alkyl group having 1 to 30 carbon atoms or an aryl group having 6 to 30 carbon atoms. Specifically, compounds having the following structural formulae may be included, however, the amide group is not limited thereto.

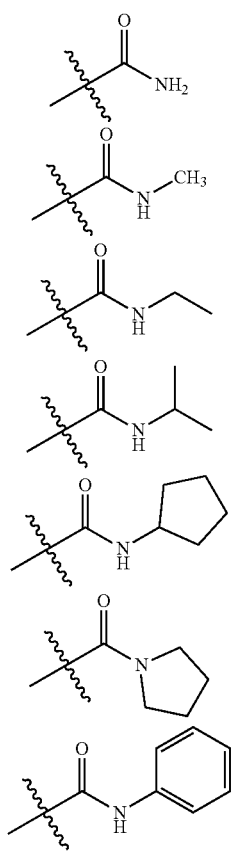

-continued

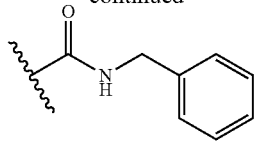

In the present specification, the number of carbon atoms of the carbonyl group is not particularly limited, but is preferably from 1 to 30. Specifically, compounds having structures as below may be included, however, the carbonyl group is not limited thereto.

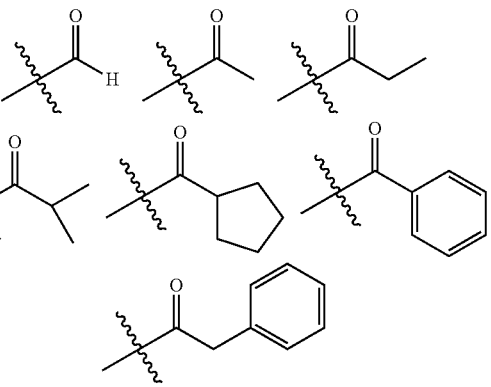

In the present specification, the ester group may be an alkyl ester group in which the oxygen of the ester group is substituted with a linear, branched or cyclic alkyl group having 1 to 25 carbon atoms; a cycloalkyl ester group in which the oxygen of the ester group is substituted with a monocyclic or polycyclic cycloalkyl group having 3 to 30 carbon atoms; or an aryl ester group in which the oxygen of the ester group is substituted with an aryl group having 6 to 30 carbon atoms. Specifically, compounds having the following structural formulae may be included, however, the ester group is not limited thereto.

In the present specification, the alkyl group may be linear or branched, and although not particularly limited thereto, the number of carbon atoms is preferably from 1 to 30. Specific examples thereof may comprise methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl and the like, but are not limited thereto.

In the present specification, the cycloalkyl group is not particularly limited, but preferably has 3 to 30 carbon atoms. Specific examples thereof may comprise cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkoxy group may be linear, branched or cyclic. The number of carbon atoms of the alkoxy group is not particularly limited, but is preferably from 1 to 30. Specific examples thereof may comprise methoxy, ethoxy, n-propoxy, isopropoxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the amine group may be selected from the group consisting of —NH$_2$; a monoalkylamine group; a dialkylamine group; an N-alkylarylamine group; a monoarylamine group; a diarylamine group; an N-arylheteroarylamine group; an N-alkylheteroarylamine group, a monoheteroarylamine group and a diheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a ditolylamine group, an N-phenyltolylamine group, a triphenylamine group, an N-phenylbiphenylamine group; an N-phenylnaphthylamine group; an N-biphenylnaphthylamine group; an N-naphthylfluorenylamine group; an N-phenylphenanthrenylamine group; an N-biphenylphenanthrenylamine group; an N-phenylfluorenylamine group; an N-phenylterphenylamine group; an N-phenanthrenylfluorenylamine group; an N-biphenylfluorenylamine group and the like, but are not limited thereto.

In the present specification, the N-alkylarylamine group means an amine group in which N of the amine group is substituted with an alkyl group and an aryl group.

In the present specification, the N-arylheteroarylamine group means an amine group in which N of the amine group is substituted with an aryl group and a heteroaryl group.

In the present specification, the N-alkylheteroarylamine group means an amine group in which N of the amine group is substituted with an alkyl group and a heteroaryl group.

In the present specification, the alkyl group in the monoalkylamine group, the dialkylamine group, the N-alkylarylamine group, the alkylthioxy group, the alkylsulfoxy group and the N-alkylheteroarylamine group is the same as the examples of the alkyl group described above. Specifically, the alkylthioxy group may comprise a methylthioxy group, an ethylthioxy group, a tert-butylthioxy group, a hexylthioxy group, an octylthioxy group and the like, and the alkylsulfoxy group may comprise mesyl, an ethylsulfoxy group, a propylsulfoxy group, a butylsulfoxy group and the like, however, the alkylthoixy group and the alkylsulfoxy group are not limited thereto.

In the present specification, specific examples of the silyl group may comprise a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the boron group may be —BR$_{100}$R$_{101}$. R$_{100}$ and R$_{101}$ are the same as or different from each other, and may be each independently selected from the group consisting of hydrogen; deuterium; halogen; a nitrile group; a substituted or unsubstituted monocyclic or polycyclic cycloalkyl group having 3 to 30 carbon atoms; a substituted or unsubstituted linear or branched alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms.

In the present specification, specific examples of the phosphine oxide group may comprise a diphenylphosphine oxide group, a dinaphthylphosphine oxide group and the like, but are not limited thereto.

In the present specification, the aryl group is not particularly limited, but preferably has 6 to 30 carbon atoms, and the aryl group may be monocyclic or polycyclic.

When the aryl group is a monocyclic aryl group, the number of carbon atoms is not particularly limited, but is preferably from 6 to 30. Specific examples of the monocyclic aryl group may comprise a phenyl group, a biphenyl group, a terphenyl group and the like, but are not limited thereto.

When the aryl group is a polycyclic aryl group, the number of carbon atoms is not particularly limited, but is preferably from 10 to 30. Specific examples of the polycyclic aryl group may comprise a naphthyl group, an anthracenyl group, a phenanthryl group, a triphenyl group, a pyrenyl group, a perylenyl group, a chrysenyl group, a fluorenyl group and the like, but are not limited thereto.

In the present specification, the fluorenyl group may be substituted, and adjacent groups may bond to each other to form a ring.

When the fluorenyl group is substituted, the following structures may be included, however, the structure is not limited thereto.

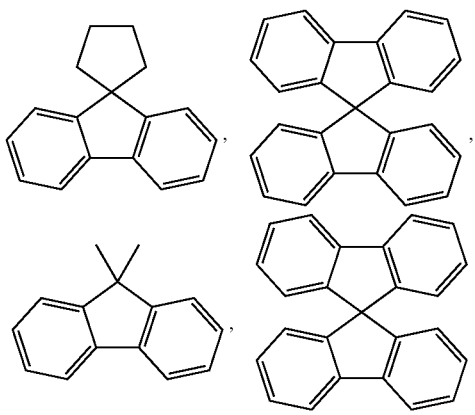

In the present specification, the "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, the aryl group in the monoarylamine group, the diarylamine group, the aryloxy group, the arylthioxy group, the arylsulfoxy group, the N-arylalkylamine group, the N-arylheteroarylamine group and the arylphosphine group is the same as the examples of the aryl group described above. Specific examples of the aryloxy group may comprise a phenoxy group, a p-tolyloxy group, an m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group and the like. Specific examples of the arylthioxy group may comprise a phenylthioxy group, a 2-methylphenylthioxy group, a 4-tert-butylphenylthioxy group and the like, and specific examples of the arylsulfoxy group may comprise a benzenesulfoxy group, a p-toluenesulfoxy group and the like. However, the aryloxy group, the arylthioxy group and the arylsulfoxy group are not limited thereto.

In the present specification, the heteroaryl group is a group comprising one or more atoms that are not carbon, that is, heteroatoms, and specifically, the heteroatom may comprise one or more atoms selected from the group consisting of O, N, Se, S and the like. The number of carbon atoms is not particularly limited, but is preferably from 2 to 30, and the heteroaryl group may be monocyclic or polycyclic. Examples of the heterocyclic group may comprise a thiophene group, a furanyl group, a pyrrole group, an imidazolyl group, a thiazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a quinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group, a thiazolyl group, an isoxazolyl group, an oxadiazolyl group, a thiadiazolyl group, a benzothiazolyl group, a phenothiazinyl group, a dibenzofuranyl group and the like, but are not limited thereto.

In the present specification, examples of the heteroaryl group in the monoheteroarylamine group, the diheteroarylamine group, the N-arylheteroarylamine group and the N-alkylheteroarylamine group are the same as the examples of the heteroaryl group described above.

In the present specification, the hydrocarbon ring may be aromatic, aliphatic or a fused ring of aromatic and aliphatic, and may be selected from among the examples of the cycloalkyl group or the aryl group except for those that are not monovalent.

In the present specification, the aromatic hydrocarbon ring may be monocyclic or polycyclic, and may be selected from among the examples of the aryl group except for those that are not monovalent.

In the present specification, the heteroring comprises one or more atoms that are not carbon, that is, heteroatoms, and specifically, the heteroatom may comprise one or more atoms selected from the group consisting of O, N, Se, S and the like. The heteroring may be monocyclic or polycyclic, may be aromatic, aliphatic or a fused ring of aromatic and aliphatic, and may be selected from among the examples of the heteroaryl group except for those that are not monovalent.

In one embodiment of the present application, Chemical Formula 1 is represented by any one of the following Chemical Formulae 2 to 4.

[Chemical Formula 2]

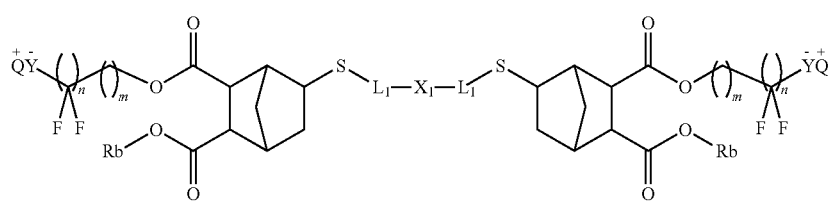

[Chemical Formula 3]

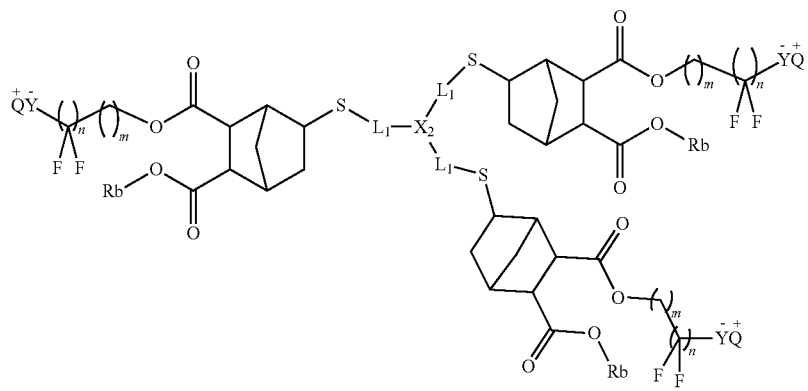

-continued

[Chemical Formula 4]

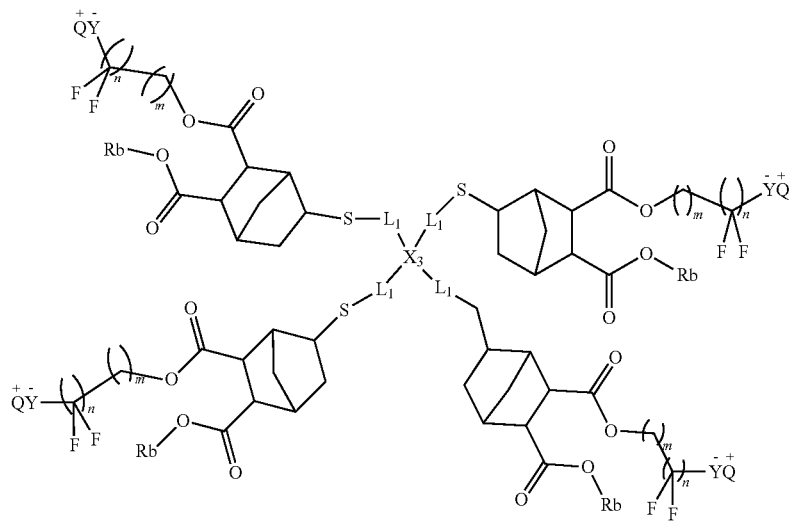

In Chemical Formulae 2 to 4, $L_1$, Rb, $Y^-$, $Q^+$, m, n and p have the same definitions as in Chemical Formula 1, $X_1$ is S; or $CR_1R_2$, $X_2$ is a substituted or unsubstituted alkyl group; or a substituted or unsubstituted aryl group, $X_3$ is a substituted or unsubstituted alkyl group, and $R_1$ and $R_2$ are the same as or different from each other, and each independently hydrogen; a substituted or unsubstituted alkyl group; a substituted or unsubstituted cycloalkyl group; a substituted or unsubstituted alkoxy group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, or adjacent groups bond to each other to form a substituted or unsubstituted aromatic hydrocarbon ring or a substituted or unsubstituted aliphatic hydrocarbon ring.

In one embodiment of the present application, X may be S; a substituted or unsubstituted aryl group; a substituted or unsubstituted heteroaryl group; or a substituted or unsubstituted alkyl group.

In one embodiment of the present application, when X is S, p may be an integer of 2.

In another embodiment, X may be S; a substituted or unsubstituted $C_6$ to $C_{60}$ aryl group; a substituted or unsubstituted $C_2$ to $C_{60}$ heteroaryl group; or a substituted or unsubstituted $C_1$ to $C_{60}$ alkyl group.

In another embodiment, X may be S; a substituted or unsubstituted $C_6$ to $C_{40}$ aryl group; a substituted or unsubstituted $C_2$ to $C_{40}$ heteroaryl group; or a substituted or unsubstituted $C_1$ to $C_{40}$ alkyl group.

In another embodiment, X may be S; a $C_6$ to $C_{40}$ aryl group; or a $C_1$ to $C_{40}$ alkyl group unsubstituted or substituted with one or more substituents selected from the group consisting of an —OH group and a $C_1$ to $C_{40}$ alkyl group.

In another embodiment, X may be S; a fluorenyl group; a phenyl group; a methyl group unsubstituted or substituted with a methyl group; or an ethyl group unsubstituted or substituted with an —OH group.

In one embodiment of the present application, $L_1$ may be a direct bond; a substituted or unsubstituted alkylene group; a substituted or unsubstituted arylene group; or a substituted or unsubstituted heteroarylene group.

In another embodiment, $L_1$ may be a direct bond; a substituted or unsubstituted $C_1$ to $C_{60}$ alkylene group; a substituted or unsubstituted $C_6$ to $C_{60}$ arylene group; or a substituted or unsubstituted $C_2$ to $C_{60}$ heteroarylene group.

In another embodiment, $L_1$ may be a direct bond; a substituted or unsubstituted $C_1$ to $C_{30}$ alkylene group; a substituted or unsubstituted $C_6$ to $C_{30}$ arylene group; or a substituted or unsubstituted $C_2$ to $C_{30}$ heteroarylene group.

In another embodiment, $L_1$ may be a direct bond; a $C_1$ to $C_{30}$ alkylene group; or a $C_6$ to $C_{30}$ arylene group.

In another embodiment, $L_1$ may be a direct bond; a phenylene group; or a methylene group.

In one embodiment of the present application, Rb may be a substituted or unsubstituted alkyl group; a substituted or unsubstituted cycloalkyl group; a substituted or unsubstituted aryl group; or a substituted or unsubstituted heteroaryl group.

In another embodiment, Rb may be a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group.

In another embodiment, Rb may be a substituted or unsubstituted $C_1$ to $C_{40}$ alkyl group; or a substituted or unsubstituted $C_3$ to $C_{40}$ cycloalkyl group.

In another embodiment, Rb may be a $C_1$ to $C_{40}$ alkyl group unsubstituted or substituted with a $C_3$ to $C_{40}$ cycloalkyl group.

In the compound provided in one embodiment of the present application, Rb is any one of the following structural formulae.

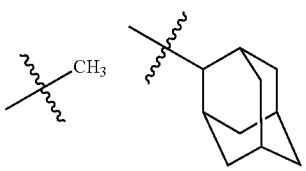

In the structural formulae,

means a site linked to Chemical Formula 1.

In one embodiment of the present application, $Q^+$ may be an onium cation.

The onium cation may be an onium cation comprising an S; I; O; N; P; Cl; Br; F; As; Se; Sn; Sb; Te; or Bi element.

In the compound provided in another embodiment, $Q^+$ is represented by the following Chemical Formula 2-1.

[Chemical Formula 2-1]

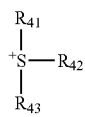

In Chemical Formula 2-1, $R_{41}$ to $R_{43}$ are the same as or different from each other, and may be each independently hydrogen; a substituted or unsubstituted alkyl group; a substituted or unsubstituted aryl group; or a substituted or unsubstituted heteroaryl group.

In one embodiment of the present application, $Y^-$ is an acid anion, and the acid anion may be one type of anion group selected from the group consisting of a sulfonic acid anion, a carboxylic acid anion, a sulfonylimide anion, a bis(alkylsulfonyl)imide anion and a tris(alkylsulfonyl)methide anion.

In one embodiment of the present application, $Y^-$ may be $-SO_3^-$.

In one embodiment of the present application, $R_{41}$ to $R_{43}$ are the same as or different from each other, and may be each independently hydrogen; a substituted or unsubstituted $C_1$ to $C_{40}$ alkyl group; a substituted or unsubstituted $C_6$ to $C_{40}$ aryl group; or a substituted or unsubstituted $C_2$ to $C_{40}$ heteroaryl group.

In another embodiment, $R_{41}$ to $R_{43}$ are the same as or different from each other, and may be each independently hydrogen; a $C_1$ to $C_{40}$ alkyl group; a $C_6$ to $C_{40}$ aryl group; or a $C_2$ to $C_{40}$ heteroaryl group.

In another embodiment, $R_{41}$ to $R_{43}$ are the same as or different from each other, and may be each independently a phenyl group.

In one embodiment of the present application, m and n may be an integer of 1 to 10.

In one embodiment of the present application, m and n may be an integer of 1.

In one embodiment of the present application, $R_1$ and $R_2$ are the same as or different from each other, and each independently hydrogen; a substituted or unsubstituted alkyl group; a substituted or unsubstituted cycloalkyl group; a substituted or unsubstituted alkoxy group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, or adjacent groups bond to each other to form a substituted or unsubstituted aromatic hydrocarbon ring or a substituted or unsubstituted aliphatic hydrocarbon ring.

In another embodiment, $R_1$ and $R_2$ are the same as or different from each other, and each independently a substituted or unsubstituted $C_6$ to $C_{60}$ aryl group, or adjacent groups bond to each other to form a substituted or unsubstituted aromatic hydrocarbon ring or a substituted or unsubstituted aliphatic hydrocarbon ring.

In another embodiment, $R_1$ and $R_2$ may bond to each other to form a substituted or unsubstituted $C_6$ to $C_{60}$ aromatic hydrocarbon ring.

In another embodiment, $R_1$ and $R_2$ may bond to each other to form a $C_6$ to $C_{60}$ aromatic hydrocarbon ring.

In another embodiment, $R_1$ and $R_2$ may bond to each other to form a $C_6$ to $C_{40}$ aromatic hydrocarbon ring.

In another embodiment, $R_1$ and $R_2$ may bond to each other to form a fluorenyl ring.

In the compound provided in one embodiment of the present application, $X_1$ of Chemical Formula 2 is represented by any one of S; and the following Chemical Formulae 1-1 to 1-3.

[Chemical Formula 1-1]

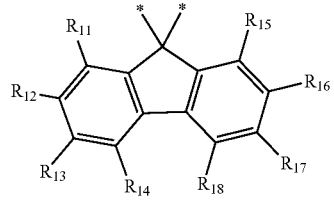

[Chemical Formula 1-2]

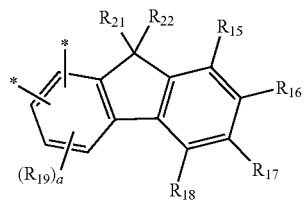

[Chemical Formula 1-3]

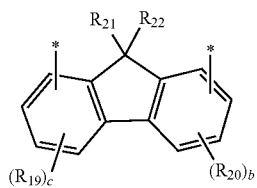

In Chemical Formulae 1-1 to 1-3,

* is a site linked to $L_1$, $R_{11}$ to $R_{22}$ are the same as or different from each other, and each independently hydrogen; a substituted or unsubstituted alkyl group; a substituted or unsubstituted cycloalkyl group; a substituted or unsubstituted alkoxy group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, or adjacent groups bond to each other to form a substituted or unsubstituted aromatic hydrocarbon ring or a substituted or unsubstituted aliphatic hydrocarbon ring, a is an integer of 0 to 2, and b and c are an integer of 0 to 3.

In one embodiment of the present application, $R_{11}$ to $R_{22}$ are the same as or different from each other, and may be each independently hydrogen; a substituted or unsubstituted alkyl group; or a substituted or unsubstituted aryl group.

In another embodiment, $R_{11}$ to $R_{22}$ are the same as or different from each other, and may be each independently hydrogen; a substituted or unsubstituted $C_1$ to $C_{40}$ alkyl group; or a substituted or unsubstituted $C_6$ to $C_{40}$ aryl group.

In another embodiment, $R_{11}$ to $R_{22}$ are the same as or different from each other, and may be each independently hydrogen; a $C_1$ to $C_{40}$ alkyl group; or a $C_6$ to $C_{40}$ aryl group.

In another embodiment, $R_{11}$ to $R_{22}$ may be hydrogen.

In the compound provided in one embodiment of the present application, $X_2$ of Chemical Formula 3 is a substituted or unsubstituted phenyl group; or $CR_{31}$, and $R_{31}$ is hydrogen; a substituted or unsubstituted alkyl group; a substituted or unsubstituted aryl group; or a substituted or unsubstituted heterocyclic group.

In another embodiment, $X_2$ of Chemical Formula 3 may be a phenyl group; or $CR_{31}$.

In one embodiment of the present application, $R_{31}$ may be hydrogen; a substituted or unsubstituted alkyl group; a substituted or unsubstituted aryl group; or a substituted or unsubstituted heterocyclic group.

In another embodiment, $R_{31}$ may be hydrogen; a substituted or unsubstituted $C_1$ to $C_{40}$ alkyl group; a substituted or unsubstituted $C_6$ to $C_{40}$ aryl group; or a substituted or unsubstituted $C_2$ to $C_{40}$ heterocyclic group.

In another embodiment, $R_{31}$ may be hydrogen; a $C_1$ to $C_{40}$ alkyl group; a $C_6$ to $C_{40}$ aryl group; or a $C_2$ to $C_{40}$ heterocyclic group.

In another embodiment, $R_{31}$ may be hydrogen; or a methyl group.

In one embodiment of the present application, $X_3$ of Chemical Formula 4 may be C; or a substituted or unsubstituted $C_1$ to $C_{10}$ alkyl group.

In another embodiment, $X_3$ of Chemical Formula 4 may be C; or a substituted or unsubstituted $C_1$ to $C_5$ alkyl group.

In another embodiment, $X_3$ of Chemical Formula 4 may be C; or a $C_1$ to $C_5$ alkyl group unsubstituted or substituted with an —OH group.

In another embodiment, $X_3$ of Chemical Formula 4 may be C; or an ethyl group unsubstituted or substituted with an —OH group.

In one embodiment of the present application, X of Chemical Formula 1 may be represented by any one of the following compounds.

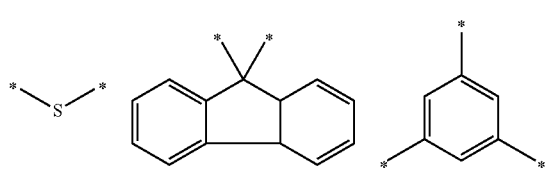

-continued

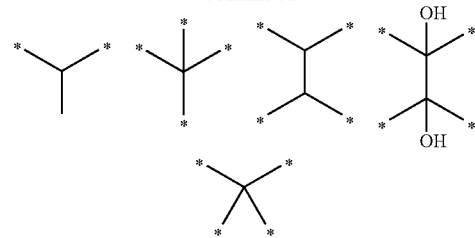

In the compounds,

means a site linked to $L_1$.

In the present application, X of Chemical Formula 1 may be represented by any one of the following compounds, and in the compounds,

means a site liked to $L_1$ present in the number of p.

One embodiment of the present application provides a photoresist composition comprising the compound of the present application; a binder resin; and a solvent.

The photoresist composition comprising the compound according to the present application is capable of high resolution and freely forming pattern shapes by comprising the compound.

The photoresist composition is used for, for example, forming a micro or nanopattern used in a process for manufacturing a microelectronic device to manufacture small electronic components when manufacturing computer chips and integrated circuits, and such a pattern-forming process is referred to as a lithography process. A lithography process using a substrate material such as a silicon-based wafer used for manufacturing an integrated circuit is generally as follows.

A thin photoresist layer is formed on a substrate using a photoresist composition coating film or a photoresist film, and then the result is baked to fix the photoresist layer on the substrate. The photoresist layer fixed on the substrate is image-wise exposed to radiation. The exposed photoresist layer is treated with a developing solution, and by dissolving and removing the exposed area of the photoresist layer, a micro or nanopattern is formed.

In one embodiment of the present application, the solvent may be one or more types selected from the group consisting of acetone, methyl ethyl ketone, methyl isobutyl ketone, methyl cellosolve, ethyl cellosolve, tetrahydrofuran, 1,4-dioxane, ethylene glycol dimethyl ether, ethylene glycol diethyl ether, propylene glycol dimethyl ether, propylene glycol diethyl ether, diethylene glycol dimethyl ether, diethylene glycol diethyl ether, diethylene glycol methyl ethyl ether, chloroform, methylene chloride, 1,2-dichloroethane, 1,1,1-trichloroethane, 1,1,2-trichloroethane, 1,1,2-trichloroethene, hexane, heptane, octane, cyclohexane, benzene, toluene, xylene, methanol, ethanol, isopropanol, propanol, butanol, t-butanol, 2-ethoxypropanol, 2-methoxypropanol, 3-methoxybutanol, cyclohexanone, cyclopentanone, propylene glycol methyl ether acetate, propylene glycol ethyl ether acetate, 3-methoxybutyl acetate, ethyl 3-ethoxypropionate, ethyl cellosolve acetate, methyl cellosolve acetate, butyl acetate, propylene glycol monomethyl ether and dipropylene glycol monomethyl ether, but is not limited thereto.

In one embodiment of the present application, specific examples of the solvent may comprise those selected from the group consisting of ketones such as γ-butyrolactone, 1,3-dimethyl-imidazolidinone, methyl ethyl ketone, cyclohexanone, cyclopentanone and 4-hydroxy-4-methyl-2-pentanone; aromatic hydrocarbons such as toluene, xylene and tetramethylbenzene; glycol ethers (cellosolve) such as ethylene glycol monoethyl ether, ethylene glycol monomethyl ether, ethylene glycol monobutyl ether, diethylene glycol monoethyl ether, diethylene glycol monomethyl ether, diethylene glycol monobutyl ether, propylene glycol monomethyl ether, propylene glycol monoethyl ether, dipropylene glycol diethyl ether and triethylene glycol monoethyl ether; ethyl acetate, butyl acetate, ethylene glycol monoethyl ether acetate, ethylene glycol monobutyl ether acetate, diethylene glycol monoethyl ether acetate, dipropylene glycol monomethyl ether acetate, ethanol, propanol, ethylene glycol, propylene glycol, carbitol, dimethylacetamide (DMAc), N,N-diethylacetamide, dimethylformamide (DMF), diethylformamide (DEF), N,N-dimethylacetamide (DMAc), N-methylpyrrolidone (NMP), N-ethylpyrrolidone (NEP), 1,3-dimethyl-2-imidazolidinone, N,N-dimethylmethoxyacetamide, dimethyl sulfoxide, pyridine, dimethyl sulfone, hexamethylphosphoramide, tetramethylurea, N-methylcaprolactam, tetrahydrofuran, m-dioxane, p-dioxane, 1,2-dimethoxyethane, bis(2-methoxyethyl)ether, 1,2-bis(2-methoxyethoxy)ethane, bis[2-(2-methoxyethoxy)]ether, and mixtures thereof.

As the solvent, propylene glycol monomethyl ether acetate (PGMEA) may be used.

In the photoresist composition included in one embodiment of the present application, the photoresist composition comprises the compound in 1 parts by weight to 10 parts by weight based on 100 parts by weight of the photoresist composition.

In another embodiment, the photoresist composition may comprise the compound in 1 parts by weight to 10 parts by weight, preferably in 1 parts by weight to 8 parts by weight, and more preferably in 1 parts by weight to 5 parts by weight based on 100 parts by weight of the photoresist composition.

In the present application, by the photoresist composition comprising the compound in the above-mentioned weight range, the compound is dissociated by an acid and thereby has increased solubility for an alkali developing solution, and as a result high resolution may be obtained.

One embodiment of the present specification provides a photoresist pattern comprising the photoresist composition according to one embodiment of the present application.

In one embodiment of the present application, the photoresist composition may be included in the photoresist pattern as it is.

One embodiment of the present application provides a photoresist pattern formed using the photoresist composition.

In one embodiment of the present application, the photoresist pattern may be formed using the following preparation method.

In one embodiment of the present specification, a photolithography process forming a photoresist pattern using the photoresist composition may comprise forming a photoresist layer on a semiconductor substrate using the photoresist composition; selectively exposing the photoresist layer; and developing the exposed photoresist layer.

One embodiment of the present application provides a method for preparing a photoresist pattern, the method comprising forming a photoresist layer by coating a photoresist composition on a semiconductor substrate; selectively exposing the photoresist layer; and developing the exposed photoresist layer.

In one embodiment of the present application, the forming of a photoresist layer comprises coating a photoresist composition on a substrate; and drying (soft baking) the coated material.

In one embodiment of the present specification, as the method of coating the photoresist composition, a method of coating with a spin coater, a bar coater, a blade coater, a curtain coater, a screen printer or the like, a method of spraying with a spray coater, or the like, may be used, however methods capable of coating a photoresist composition may be used without limit.

In the drying (soft baking) of the coated material, the coated material may be dried under a condition of 30 seconds to 120 seconds at 70° C. to 200° C. The drying method may comprise, for example, an oven, a hot plate, vacuum drying and the like, but is not limited thereto. When going through the drying, a solvent is removed from the photoresist composition increasing adhesive strength between the wafer and the photosensitive resin layer, and the photoresist layer may be formed on the semiconductor substrate.

In one embodiment of the present application, the selectively exposing of the photoresist layer is aligning a mask on the photoresist, and exposing an area of the photoresist layer not covered by the mask to ultraviolet rays. The mask may be in contact with the photoresist layer, or may also be aligned at a certain distance from the photoresist layer.

In the exposure process, a light source irradiated as a light irradiation means may comprise electromagnetic waves, extreme ultraviolet rays (EUV), from ultraviolet rays to visible rays, an electron beam, X-rays, laser rays and the like. In addition, as a method of irradiating the light source, known means such as a high pressure mercury lamp, a xenon lamp, a carbon arc lamp, a halogen lamp, a cold cathode tube for a copier, an LED and a semiconductor laser may be used.

In one embodiment of the present application, the selectively exposing of the photoresist layer may further comprise heating (post-exposure baking) the exposed photoresist layer after the exposure. By heating the exposed photoresist layer, components in the photoresist composition are realigned, reducing a standing wave of the photoresist layer.

The heating (post-exposure baking) of the photoresist layer may be conducted under a condition of 30 seconds to 2 minutes at 70° C. to 150° C.

In one embodiment of the present application, the developing of the exposed photoresist layer is removing the exposed portion in the photoresist layer by immersing in a developing solution. As the developing method, photoresist developing methods known in the art such as a rotary spray method, a paddle method or an immersion method accompanying ultrasonic treatment may be used, however, the method is not limited thereto.

Examples of the developing solution may comprise alkali metal or alkaline earth metal hydroxides, carbonates, hydrogen carbonates, an aqueous basic solution such as an ammonia water quaternary ammonium salt may be used. Among these, an aqueous ammonia quaternary ammonium solution such as an aqueous tetramethyl ammonium solution is particularly preferred.

Through steps as above, the photoresist pattern according to one embodiment of the present application may be formed.

In one embodiment of the present disclosure, the method for forming a pattern of a photoresist layer may be used in a semiconductor manufacturing process.

Specifically, in one embodiment of the semiconductor manufacturing process, a process of etching an area of the semiconductor substrate not covered by the photoresist layer, and removing (ashing) the photoresist layer from the semiconductor substrate is further included in the photolithography process.

The etching of an area of the semiconductor substrate not covered by the photoresist layer is etching the semiconductor substrate area other than the pattern of the photoresist layer.

The removing of the photoresist layer from the semiconductor substrate may use known methods, and for example, may be conducted by heating a wafer in a low pressure state using a reaction chamber, and then injecting a plasma comprising an oxygen group or an oxygen ion thereto.

The semiconductor substrate is not limited, and those known in the art may be used. For example, substrates for electronic components, or those having a predetermined wiring pattern formed thereon may be included as an example. Examples of the substrate for an electronic component may comprise substrates made of metal or glass substrates such as silicon, silicon nitride, titanium, tantalum, palladium, titanium tungsten, copper, chromium, iron, aluminum, gold and nickel, or the like. Examples of the wiring pattern material may comprise copper, solder, chromium, aluminum, nickel, gold and the like, but are not limited thereto.

One embodiment of the present specification provides an electronic device comprising the photoresist pattern.

The electronic device may be used without limit as long as it is capable of using a photoresist layer prepared from the composition according to the present specification. For example, it may be used in a wide range of applications such as circuit substrate manufacturing, electronic component manufacturing, connection terminals such as bumps or metal posts, and wiring patterns.

[Mode for Disclosure]

Hereinafter, the present specification will be described in detail with reference to examples in order to specifically describe the present specification. However, the examples according to the present specification may be modified to various other forms, and the scope of the present specification is not to be construed as being limited to the examples described below. Examples of the present specification are provided in order to more fully describe the present specification to those having average knowledge in the art.

PREPARATION EXAMPLE

Preparation Example 1—<Preparation of Compound 3>

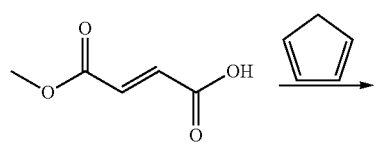

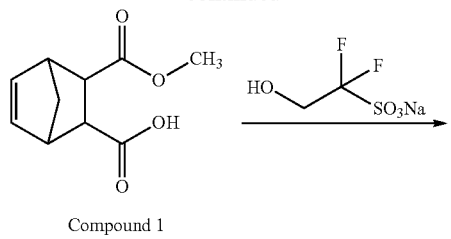

Compound 1

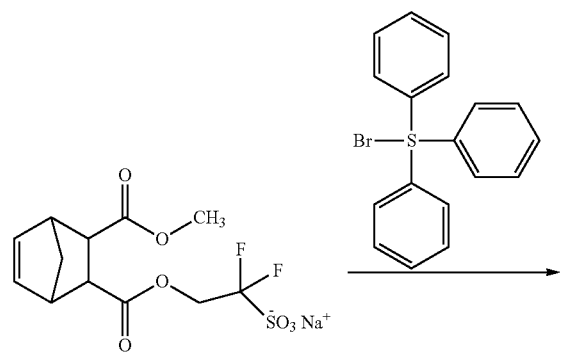

Compound2

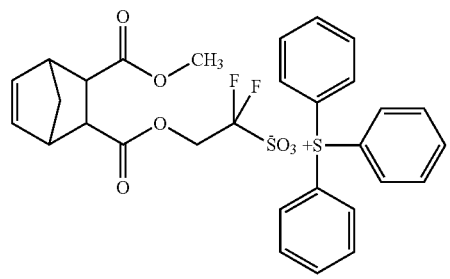

Compound3

Cyclopentadiene (132.2 g, 2.0 mol), 2-carboxyethyl acrylate (130.1 g, 1.0 mol) and 4-methoxyphenol (2.4 g, 0.02 mol) were introduced to a high pressure reactor, and the result was reacted for 18 hours at 180° C., and then vacuum distilled to obtain Compound 1 (190 g, 97%).

Compound 1 (196 g, 1.0 mol), sodium 1,1-difluoro-2-hydroxyethane-1-sulfonate (220.9 g, 1.2 mol) and $H_2SO_4$ (19.6 g, 0.2 mol) were introduced and reacted for 6 hours at 60° C. After the reaction was finished, $H_2O$ (1 L) was introduced thereto, the result was extracted 3 times with ethyl acetate (1 L), and the solvent was removed. The obtained result was recrystallized with ethanol (EtOH) to obtain Compound 2 (330 g, 91%).

Compound 2 (181 g, 0.5 mol) and triphenylsulfonium bromide (172 g, 0.5 mol) were introduced to a $H_2O$:dichloromethane=1:1 solution (1 L), and reacted for 12 hours at room temperature (25° C.). After the reaction was finished, the organic layer was washed 3 times with $H_2O$ (1 L), and then diethyl ether was introduced thereto to form precipitates. The precipitates were filtered and then dried to obtain Compound 3 (280 g, 93%).

Synthesis identification data of Compound 3 are as follows.

1H-NMR (DMSO-D6): (ppm) δ=7.4-7.3 (m, 15H), 6.1-6.0 (m, 2H), 4.5-4.3 (m, 2H), 3.8-3.5 (m, 5H), 3.1-2.9 (m, 2H), 1.8-1.4 (m, 2H)

Preparation Example 2—<Preparation of Compound 7>

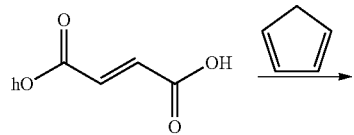

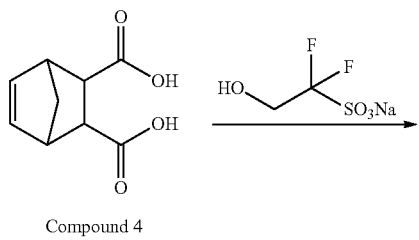

Compound 4

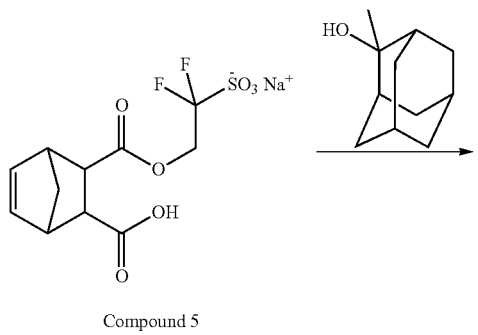

Compound 5

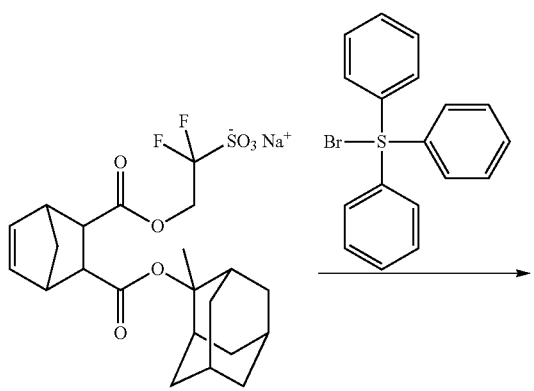

Compound 6

-continued

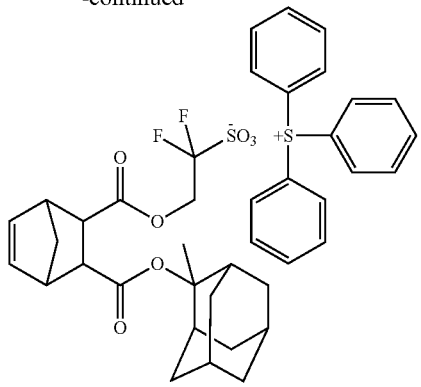

Compound 7

After moderately dissolving fumaric acid (117 g, 1 mol) in tetrahydrofuran (THF), cyclopentadiene (198 g, 3 mol) was injected thereto over 30 minutes at 0° C. using a dropping funnel, and the result was stirred for 12 hours at room temperature. The residual cyclopentadiene was removed through vacuum distillation to obtain Compound 4 (173 g, 95%).

Compound 4 (164 g, 0.9 mol), sodium 1,1-difluoro-2-hydroxyethane-1-sulfonate (166 g, 0.9 mol) and sulfuric acid (19 g, 0.18 mol) were introduced and stirred for 6 hours at 60° C. After the reaction was completed, the layers were separated using ethyl acetate, and the solvent was evaporated to obtain a product. The obtained product was dissolved in ethanol for recrystallization, and as a result, Compound 5 (298 g, 95%) was obtained.

Dichloromethane (1050 mL), 2-methyl-2-adamantanol (50 g, 0.3 mol) and triethylamine (TEA) (67 g, 0.66 mol) were introduced to a flask, and stirred. A solution dissolving Compound 5 (105 g, 0.3 mol), 1-ethyl-3-(3-dimethylaminopropyl)carbodiimide (EDCI) (56 g, 0.36 mol) and 1-hydroxybenzotriazole hydrate (HOBT) (56 g, 0.36 mol) in dichloromethane (10 ml per 1 gram) was slowly added dropwise thereto using a dropping funnel. The result was reacted for approximately 5 hours at room temperature, and extracted with dichloromethane while washing with citric acid and brine, and separated. The result was MgSO$_4$ treated and dried to obtain Compound 6 (144 g, 97%).

Compound 6 (125 g, 0.25 mol) and triphenylsulfonium bromide (86 g, 0.25 mol) were introduced to a H$_2$O:dichloromethane=1:1 solution (1 L), and reacted for 12 hours at room temperature (25° C.). After the reaction was finished, the organic layer was washed 3 times with H$_2$O (1 L), diethyl ether was introduced thereto to form precipitates, and the precipitates were filtered and dried to obtain Compound 7 (171 g, 93%).

Synthesis identification data of Compound 7 are as follows.

1H-NMR (DMSO-D6): (ppm) δ=7.5-7.0 (m, 15H), 6.1-6.0 (m, 2H), 4.5-4.3 (m, 2H), 3.8-3.5 (m, 5H), 3.1-2.9 (m, 2H), 2.7-2.4 (m, 2H), 1.8-1.6 (m, 5H), 1.5-1.3 (m, 7H), 1.2-0.9 (m, 5H)

Preparation Example 3—<Preparation of Compound 8>

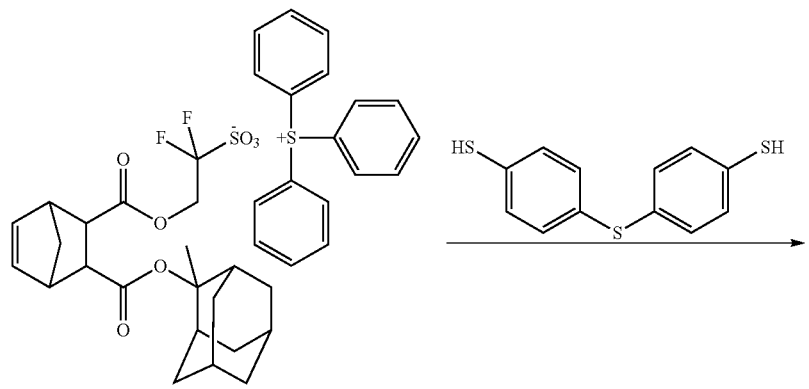

Compound 7

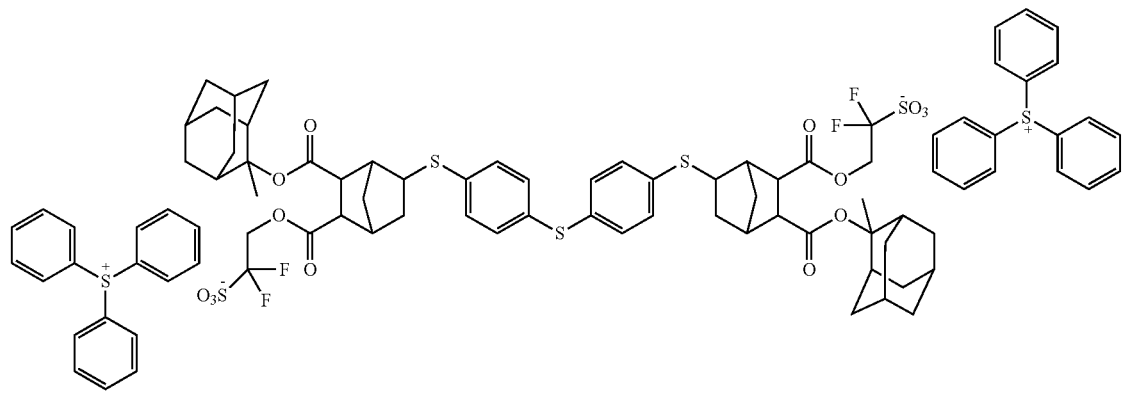

Compound 8

Compound 7 (386.45 g) synthesized in Preparation Example 2, AlBN (32.84 g) and 4,4'-thiodibenzenethiol (62.60 g) were introduced to a reaction flask. The result was thiol-ene click reacted for 3 hours at 65° C., a temperature that is the same as the polymerization temperature, to prepare Compound 8 in which the above-mentioned compounds were mutually bonded through a functional group comprising ethylene sulfide. When the reaction was completed, the temperature was lowered to room temperature (25° C.), the result was diluted with IPA and PGMEA, and poured into water to collect precipitates. The polymer obtained through filtration was poured again into a mixed solvent of IPA and PGMEA to collect precipitates, and the precipitates were filtered, and then dried for one day in a 40° C. oven.

Synthesis identification data of Compound 8 are as follows.

1H-NMR (DMSO-D6): (ppm) δ=7.6-7.0 (m, 38H), 5.3-4.9 (m, 4H), 2.9-2.5 (m, 10H), 2.4-2.3 (m, 2H), 2.2-2.0 (m, 4H), 1.9-0.9 (m, 36H)

Preparation Example 4—<Preparation of Compound 9>

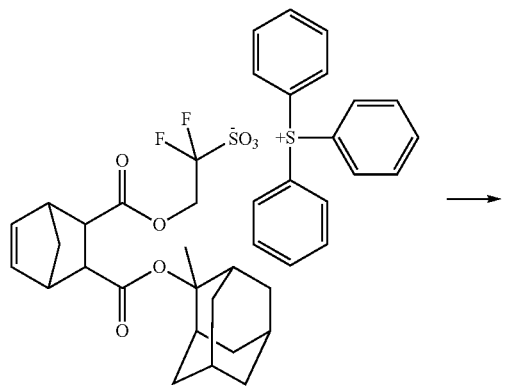

Compound 7

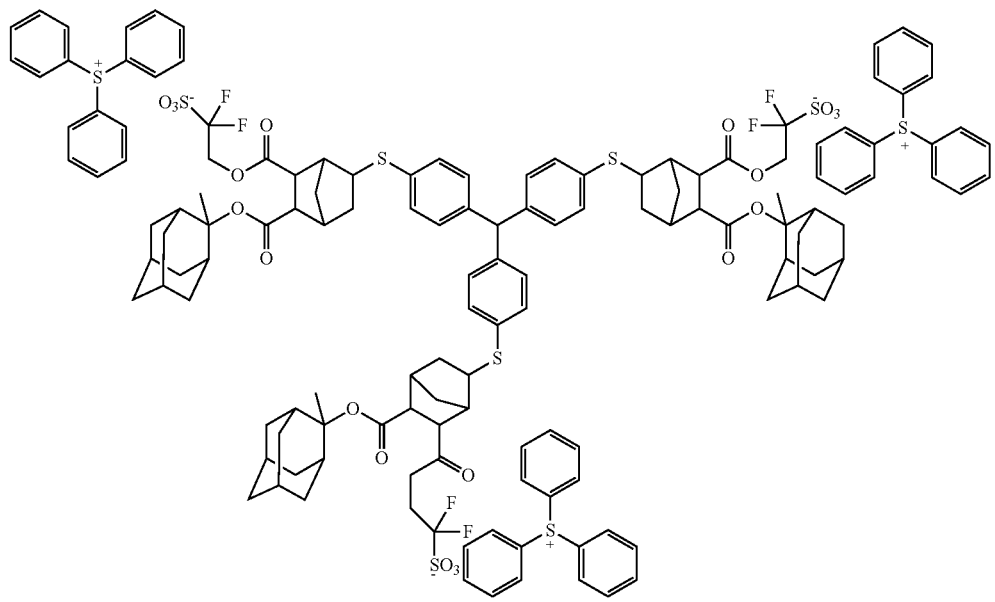

Compound 9

Compound 7 (386.45 g) synthesized in Preparation Example 2, AIBN (32.84 g) and 4,4',4''-methanetriyltribenzenethiol (56.76 g) were introduced to a reaction flask. The result was thiol-ene click reacted for 3 hours at 65° C., a temperature that is the same as the polymerization temperature, to prepare Compound 9 in which the above-mentioned compounds were mutually bonded through a functional group comprising ethylene sulfide. When the reaction was completed, the temperature was lowered to room temperature (25° C.), the result was diluted with IPA and PGMEA, and poured into water to collect precipitates. The polymer obtained through filtration was poured again into a mixed solvent of IPA and PGMEA to collect precipitates, and the precipitates were filtered, and then dried for one day in a 40° C. oven.

Synthesis identification data of Compound 9 are as follows.

1H-NMR (DMSO-D6): (ppm) δ=7.6-7.0 (m, 57H), 5.6-5.4 (m, 1H), 4.6-4.1 (m, 6H), 2.9-2.5 (m, 15H), 2.4-2.3 (m, 3H), 2.2-2.0 (m, 6H), 1.9-0.9 (m, 54H)

Preparation Example 5—<Preparation of Compound 10>

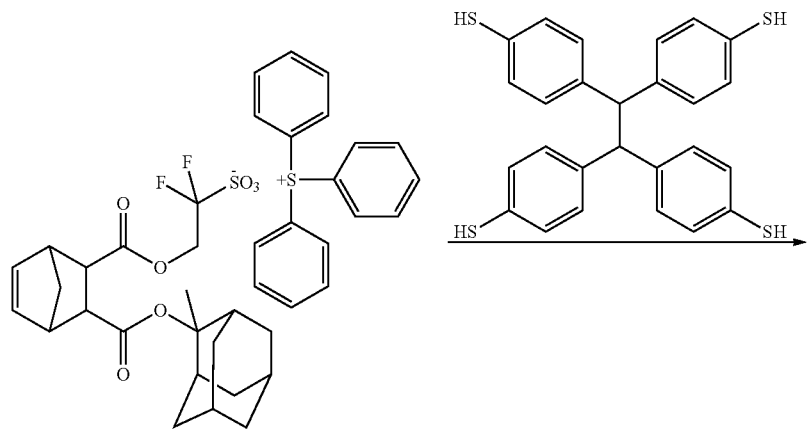

Compound 7

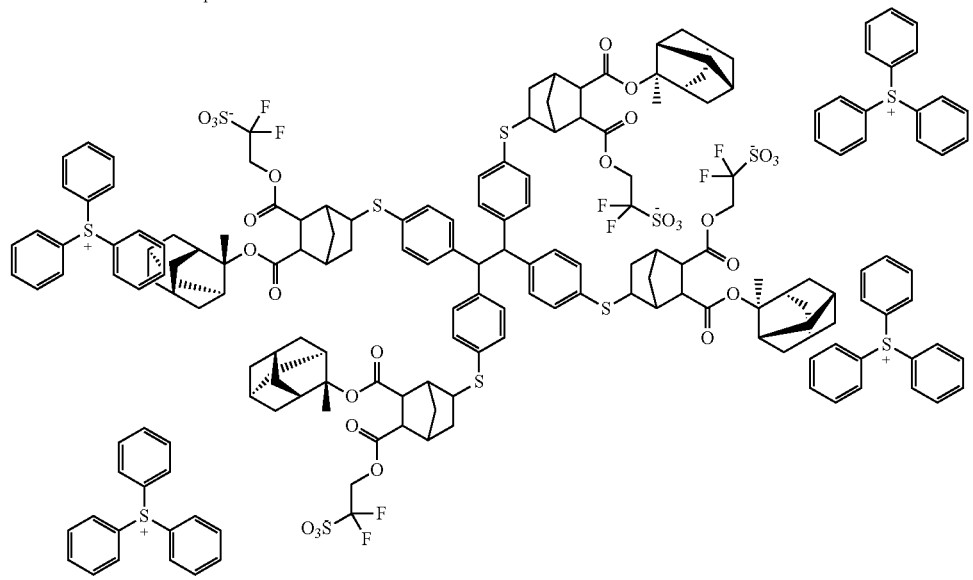

Compound 10

Compound 7 (386.45 g) synthesized in Preparation Example 2, AIBN (32.84 g) and 4,4',4",4'''-(ethane-1,1,2,2-tetrayl)tetrabenzenethiol (115.68 g) were introduced to a reaction flask. The result was thiol-ene click reacted for 3 hours at 65° C., a temperature that is the same as the polymerization temperature, to prepare Compound 10 in which the above-mentioned compounds were mutually bonded through a functional group comprising ethylene sulfide. When the reaction was completed, the temperature was lowered to room temperature (25° C.), the result was diluted with IPA and PGMEA, and poured into water to collect precipitates. The polymer obtained through filtration was poured again into a mixed solvent of IPA and PGMEA to collect precipitates, and the precipitates were filtered, and then dried for one day in a 40° C. oven.

Synthesis identification data of Compound 10 are as follows.

1H-NMR (DMSO-D6): (ppm) δ=7.6-7.0 (m, 76H), 4.6-4.1 (m, 10H), 2.9-2.5 (m, 20H), 2.4-2.3 (m, 4H), 2.2-2.0 (m, 8H), 1.9-0.9 (m, 72H)

Preparation Example 6—<Preparation of Polymer 1>

Compound 3 (301.33 g, 0.5 mol) synthesized in Preparation Example 1 was introduced to a reaction flask, and anisole (150.67 g, 50 wt %) was introduced thereto. The result was stirred for 20 minutes under the nitrogen atmosphere. A palladium metal catalyst was dissolved in anisole under the argon atmosphere to prepare a palladium catalyst solution. After heating the reaction solution to 65° C., the prepared palladium metal catalyst solution was injected thereto using a syringe, and the result was stirred for 18 hours. After the reaction was finished, the reaction solution was diluted with anisole, and introduced to an excess amount of hexane to collect precipitates. Solids obtained as above were filtered, and dried for 18 hours in a 40° C. oven to obtain Polymer 1. A weight average molecular weight of Polymer 1 measured using gel permeation chromatography (GPC) was 4,300 g/mol.

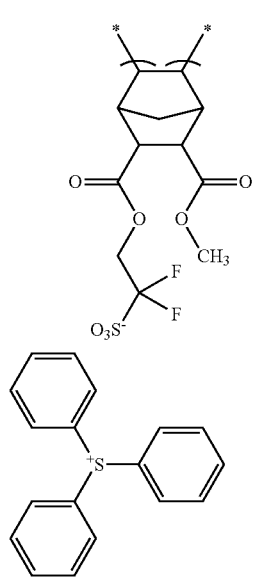

Polymer 1

Preparation Example 7—<Preparation of Polymer 2>

Compound 7 (386.45 g, 0.5 mol) synthesized in Preparation Example 2 was introduced to a reaction flask, and anisole (184.22 g, 50 wt %) was introduced thereto. The result was stirred for 20 minutes under the nitrogen atmosphere. A palladium metal catalyst was dissolved in anisole under the argon atmosphere to prepare a palladium catalyst solution. After heating the reaction solution to 65° C., the prepared palladium metal catalyst solution was injected thereto using a syringe, and the result was stirred for 18 hours. After the reaction was finished, the reaction solution was diluted with anisole, and introduced to an excess amount of hexane to collect precipitates. Solids obtained as above were filtered, and dried for 18 hours in a 40° C. oven to obtain Polymer 2. A weight average molecular weight of Polymer 2 measured using gel permeation chromatography (GPC) was 4,500 g/mol.

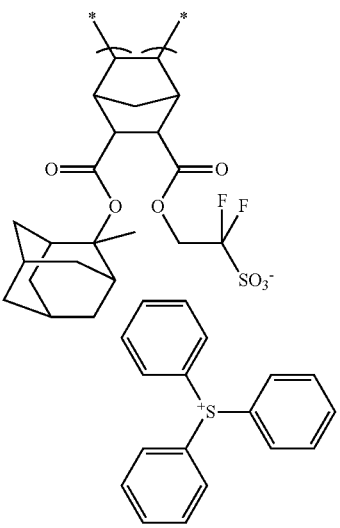

Polymer 2

Preparation Example 8—<Preparation of Compound 11>

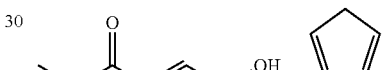

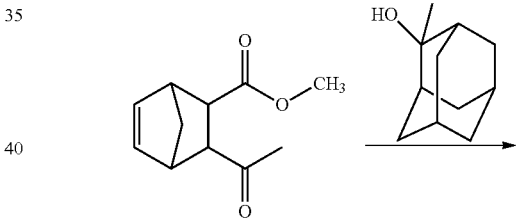

Compound 1

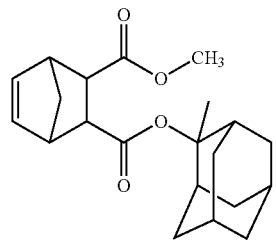

Compound 11

Cyclopentadiene (132.2 g, 2.0 mol), 2-carboxyethyl acrylate (130.1 g, 1.0 mol) and 4-methoxyphenol (2.4 g, 0.02 mol) were introduced to a high pressure reactor, reacted for 18 hours at 180° C., and then vacuum distilled to obtain Compound 1 (190 g, 97%).

Dichloromethane (1050 mL), 2-methyl-2-adamantanol (50 g, 0.3 mol) and triethylamine (TEA) (67 g, 0.66 mol) were introduced to a flask, and stirred. A solution dissolving Compound 1 (59 g, 0.3 mol), 1-ethyl-3-(3-dimethylaminopropyl)carbodiimide (EDCI) (56 g, 0.36 mol) and 1-hydroxybenzotriazole hydrate (HOBT) (56 g, 0.36 mol) in dichloromethane (10 ml per 1 gram) was slowly added dropwise thereto using a dropping funnel. The result was reacted for approximately 5 hours at room temperature, and extracted with dichloromethane while washing with citric acid and brine, and separated. The result was MgSO$_4$ treated and dried to obtain Compound 11 (144 g, 97%).

Synthesis identification data of Compound 11 are as follows.

1H-NMR (DMSO-D6): (ppm) δ=6.1-6.0 (m, 2H), 3.7-3.6 (m, 5H), 3.1-3.0 (m, 2H), 2.6-2.5 (m, 2H), 1.8-1.3 (m, 12H), 1.2-1.0 (m, 5H)

Preparation Example 9—<Preparation of Polymer 3>

Compound 11 (172.23 g, 0.5 mol) synthesized in Preparation Example 8 was introduced to a reaction flask, and anisole (150.67 g, 50 wt %) was introduced thereto. The result was stirred for 20 minutes under the nitrogen atmosphere. A palladium metal catalyst was dissolved in anisole under the argon atmosphere to prepare a palladium catalyst solution. After heating the reaction solution to 65° C., the prepared palladium metal catalyst solution was injected thereto using a syringe, and the result was stirred for 18 hours. After the reaction was finished, the reaction solution was diluted with anisole, and introduced to an excess amount of hexane to collect precipitates. Solids obtained as above were filtered, and dried for 18 hours in a 40° C. oven to obtain Polymer 3. A weight average molecular weight of Polymer 3 measured using gel permeation chromatography (GPC) was 3,800 g/mol.

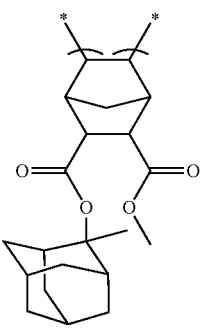

Polymer 3

Preparation Example of Photoresist Composition

Example 1

A mixture solution having a solid content (comprising resin and quencher) of 4% was prepared by adding Compound 8 prepared in Preparation Example 3 as a resin, N-tert-amyloxycarbonyl-4-hydroxypiperidine that is a quencher in 0.5 mass % with respect to the total mass of the resin, and propylene glycol monomethyl ether acetate (PGMEA) as a solvent. The obtained mixture solution was filtered using a 0.1 μm filter to obtain a resist solution (composition).

Examples 2 and 3

Examples 2 and 3 were prepared in the same manner as the preparation method of Example 1 except that constituents were changed as in the following Table 1.

Comparative Example 1

A mixture solution having a solid content (comprising resin, photoacid generator and quencher) of 4% was prepared by adding Polymer 1 prepared in Preparation Example 6 as a resin, sulfonium, [4-(1,1-dimethylethyl)phenyl]diphenyl-, salt with 1-tricyclo[3.3.1.13,7]dec-1-yl 2,2-difluoro-2-sulfoacetate (1:1) in 2.0 mass % with respect to the total mass of the resin as a photoacid generator, N-tert-amyloxycarbonyl-4-hydroxypiperidine that is a quencher in 0.5 mass % with respect to the total mass of the resin, and propylene glycol monomethyl ether acetate (PGMEA) as a solvent. The obtained mixture solution was filtered using a 0.1 μm filter to obtain a resist solution (composition).

Comparative Example 2

Comparative Example 2 was prepared in the same manner as the preparation method of Comparative Example 1 except that constituents were changed as in the following Table 1.

Comparative Example 3

Comparative Example 3 was prepared in the same manner as the preparation method of Comparative Example 1 except that constituents were changed as in the following Table 1.

TABLE 1

| | Resin | PAG (Mass % with Respect to Total Mass of Resin) | Q1 (Mass % with Respect to Total Mass of Resin) |
|---|---|---|---|
| Example 1 | Compound 8 | — | 0.5 |
| Example 2 | Compound 9 | — | 0.5 |
| Example 3 | Compound 10 | — | 0.5 |
| Comparative Example 1 | Polymer 1 | 2.0 | 0.5 |
| Comparative Example 2 | Polymer 2 | 2.0 | 0.5 |
| Comparative Example 3 | Polymer 3 | 2.0 | 0.5 |

Experimental Example

Preparation of Photoresist Layer

After forming an anti-reflection film on a silicon wafer, each of the resist solutions (Examples 1 to 3 and Comparative Examples 1 to 3) was spin coated. The result was baked (SOB) for 60 seconds at 120° C. using a hot plate to form a photoresist layer.

An electron beam was irradiated thereon to conduct patterning. The result was baked (PEB) for 90 seconds at 110° C. for acid diffusion, and developed for 60 seconds using a 2.38% aqueous tetramethylammonium hydroxide (TMAH) solution. The thickness of the prepared resist film was from 30 nm to 32 nm when measured using a scanning electron microscope (SEM).

Evaluation of Photoresist Layer Optimum Exposure (Dose) and Line Width Roughness (LWR)

For each of the compositions of Examples 1 to 3 and Comparative Examples 1 to 3, photoresist dose and line width roughness (LWR) were evaluated as follows.

The evaluation condition was 120° C./60 s for SOB, and 110° C./90 s for PEB.

SOB is soft bake meaning a step of baking before exposure, and is normally a step for removing a solvent remining in a photoresist layer after coating the photoresist layer.

PEB is post exposure bake meaning a step of baking after exposure, and PEB was conducted after the exposure for acid diffusion.

The evaluation results are described in the following Table 2. Specifically, dose means optimum exposure, and the exposure at which the line dimension width was 40 nm when observed using an electron microscope for a 32 nm 1:1 line & space pattern was employed as dose.

The results are shown in the following Table 2 such that 50 mJ/cm² or less (☉), 70 mJ/cm² or less (○), 90 mJ/cm² or less (Δ), and greater than 90 mJ/cm² (X).

In addition, LWR means line width roughness, and fluctuations in the line width of the line in a 32 nm 1:1 line & space were measured using a scanning electron microscope (SEM). The results are shown in the following Table 2 such that 7 nm or less (☉), 10 nm or less (○), 13 nm or less (Δ), and greater than 13 nm (X).

TABLE 2

|  | Dose | | LWR | |
| --- | --- | --- | --- | --- |
|  | mJ/cm² | Evaluation | nm | Evaluation |
| Example 1 | 61 | ○ | 7.9 | ○ |
| Example 2 | 48 | ☉ | 8.5 | ○ |
| Example 3 | 41 | ☉ | 6.9 | ☉ |
| Comparative Example 1 | 105 | X | 12.8 | Δ |
| Comparative Example 2 | 89 | Δ | 12.6 | X |
| Comparative Example 3 | 120 | X | 14.3 | X |

As seen from Table 2, it was identified that Examples 1 to 3 were more useful for micropattern preparation compared to Comparative Examples 1 to 3 due to low dose. This is due to the fact that the photoacid generator generated by the exposure was capable of immediately deprotecting substituents in the adjacent resin leading to higher sensitivity than existing resists, and as a result, a high resolution pattern was obtained even with small exposure. In addition, in Examples 1 to 3, the resin in the photoresist was formed with monomers, and it was identified that line width roughness (LWR) was improved by having the resin in the photoresist formed with monomers instead of polymers.

In addition, it was identified that Examples 1 to 3 had lower line width roughness (LWR) compared to Comparative Examples 1 to 3, and a micro photoresist pattern was formed. Furthermore, as seen in Examples 1 to 3, the compound according to one embodiment of the present application comprises a compound having $SO_3^-$ and $S^+$ ionic groups, and poor evaluation results were identified in Comparative Example 3 not comprising the compound since the function as a photoacid generator was not fulfilled.

The invention claimed is:

1. A compound represented by Chemical Formula 1:

[Chemical Formula 1]

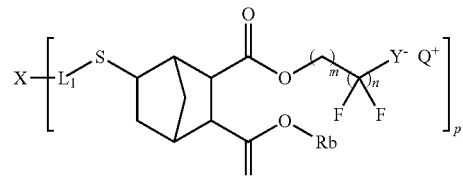

wherein, in the Chemical Formula 1, p is an integer of 2 to 4;

X is S, a substituted or unsubstituted aryl group, a substituted or unsubstituted heteroaryl group or a substituted or unsubstituted alkyl group, provided that when p is an integer of 3 or 4, X is not S;

$L_1$ is the same as or different from each other and each independently is a direct bond, a substituted or unsubstituted alkylene group, a substituted or unsubstituted arylene group, or a substituted or unsubstituted heteroarylene group;

Rb is the same as or different from each other and each independently is a substituted or unsubstituted alkyl group, a substituted or unsubstituted cycloalkyl group, a substituted or unsubstituted aryl group, or a substituted or unsubstituted heteroaryl group;

$Q^+$ is the same as or different from each other and each independently is an onium cation;

$Y^-$ is the same as or different from each other and each independently is an acid anion; and m and n are each an integer of 1 to 10.

2. The compound of claim 1, wherein the compound is represented by any one of Chemical Formulae 2 to 4:

[Chemical Formula 2]

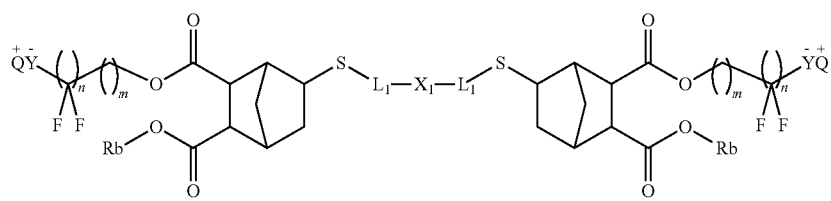

-continued

[Chemical Formula 3]

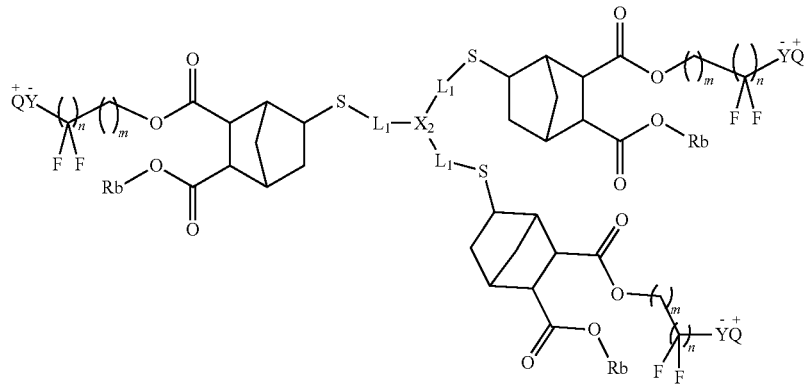

[Chemical Formula 4]

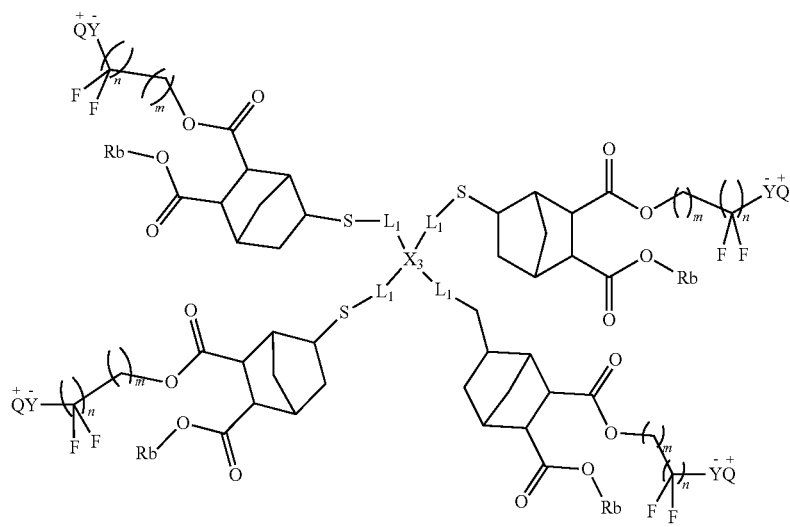

in the Chemical Formulae 2 to 4, $L_1$, Rb, $Y^-$, $Q^+$, m and n are as defined in claim 1;

$X_1$ is S or $CR_1R_2$;

$X_2$ is a substituted or unsubstituted alkyl group or a substituted or unsubstituted aryl group;

$X_3$ is C or a substituted or unsubstituted alkyl group; and $R_1$ and $R_2$ are the same as or different from each other, and each independently hydrogen, a substituted or unsubstituted alkyl group, a substituted or unsubstituted cycloalkyl group, a substituted or unsubstituted alkoxy group, a substituted or unsubstituted silyl group, a substituted or unsubstituted boron group, a substituted or unsubstituted amine group, a substituted or unsubstituted arylphosphine group, a substituted or unsubstituted phosphine oxide group, a substituted or unsubstituted aryl group, a substituted or unsubstituted heteroaryl group, or adjacent groups bond to each other to form a substituted or unsubstituted aromatic hydrocarbon ring or a substituted or unsubstituted aliphatic hydrocarbon ring.

3. The compound of claim 2, wherein $X_1$ of the Chemical Formula 2 is S or represented by any one of Chemical Formulae 1-1 to 1-3:

[Chemical Formula 1-1]

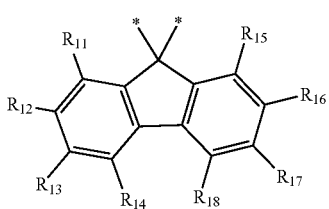

[Chemical Formula 1-2]

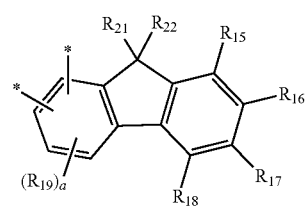

[Chemical Formula 1-3]

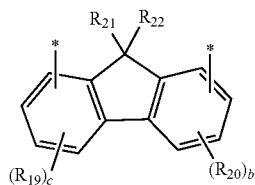

in the Chemical Formulae 1-1 to 1-3,

* is a site linked to $L_1$;

$R_{11}$ to $R_{22}$ are the same as or different from each other, and each independently hydrogen, a substituted or unsubstituted alkyl group, a substituted or unsubstituted cycloalkyl group, a substituted or unsubstituted alkoxy group, a substituted or unsubstituted silyl group, a substituted or unsubstituted boron group, a substituted or unsubstituted amine group, a substituted or unsubstituted arylphosphine group, a substituted or unsubstituted phosphine oxide group, a substituted or unsubstituted aryl group, a substituted or unsubstituted heteroaryl group, or adjacent groups bond to each other to form a substituted or unsubstituted aromatic hydrocarbon ring or a substituted or unsubstituted aliphatic hydrocarbon ring;

a is an integer of 0 to 2; and b and c are an integer of 0 to 3.

4. The compound of claim 2, wherein $X_2$ of the Chemical Formula 3 is a substituted or unsubstituted phenyl group, or $CR_{31}$, and wherein $R_{31}$ is hydrogen, a substituted or unsubstituted alkyl group, a substituted or unsubstituted aryl group, or a substituted or unsubstituted heterocyclic group.

5. The compound of claim 2, wherein $X_3$ of the Chemical Formula 4 is C; or a substituted or unsubstituted $C_1$ to $C_{10}$ alkyl group.

6. The compound of claim 1, wherein Rb is any one of the following structural formulae:

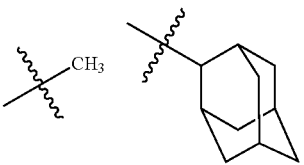

in the structural formulae,

means a site linked to the Chemical Formula 1.

7. The compound of claim 1, wherein $Q^+$ is an onium cation comprising an S, I, O, N, P, Cl, Br, F, As, Se, Sn, Sb, Te, or Bi element.

8. The compound of claim 1, wherein $Q^+$ is represented by Chemical Formula 2-1:

[Chemical Formula 2-1]

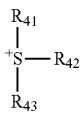

in the Chemical Formula 2-1, $R_{41}$ to $R_{43}$ are the same as or different from each other, and each independently hydrogen, a substituted or unsubstituted alkyl group, a substituted or unsubstituted aryl group, or a substituted or unsubstituted heteroaryl group.

9. A photoresist composition comprising:
the compound of claim 1;
a binder resin; and
a solvent.

10. The photoresist composition of claim 9 comprising the compound in 1 parts by weight to 10 parts by weight based on 100 parts by weight of the photoresist composition.

11. A photoresist pattern comprising the photoresist composition of claim 9.

12. A method for preparing a photoresist pattern, the method comprising:
forming a photoresist layer by coating the photoresist composition of claim 9 on a semiconductor substrate;
selectively exposing the photoresist layer; and
developing the exposed photoresist layer.

13. The method for preparing a photoresist pattern of claim 12, wherein the selectively exposing of the photoresist layer is aligning a mask on the photoresist, and exposing an area of the photoresist layer not covered by the mask to ultraviolet rays.

14. The method for preparing a photoresist pattern of claim 12, wherein the developing of the exposed photoresist layer is removing the exposed portion in the photoresist layer by immersing in a developing solution.

* * * * *